US007326196B2

(12) United States Patent
Olsen et al.

(10) Patent No.: US 7,326,196 B2
(45) Date of Patent: Feb. 5, 2008

(54) CATHETER ASSEMBLIES FOR CONTROLLED MOVEMENT OF FLUID

(75) Inventors: Raymond E. Olsen, Smithfield, UT (US); T. Wade Fallin, Hyde Park, UT (US); Daniel E. Gerbec, Logan, UT (US); Marc C. Yap, Millville, UT (US)

(73) Assignee: Breg, Inc., Vista, CA (US)

( * ) Notice: Subject to any disclaimer, the term of this patent is extended or adjusted under 35 U.S.C. 154(b) by 13 days.

(21) Appl. No.: 10/270,091

(22) Filed: Oct. 14, 2002

(65) Prior Publication Data

US 2004/0073194 A1    Apr. 15, 2004

(51) Int. Cl.
*A61M 25/00* (2006.01)
*A61M 25/16* (2006.01)
*A61M 5/178* (2006.01)

(52) U.S. Cl. .................. 604/523; 604/537; 604/164.02
(58) Field of Classification Search ........ 604/523–537, 604/164.01, 164.02, 164.09, 164.11, 164.04
See application file for complete search history.

(56) References Cited

U.S. PATENT DOCUMENTS

| | | | |
|---|---|---|---|
| 4,692,153 A | 9/1987 | Berlin et al. | |
| 4,706,671 A * | 11/1987 | Weinrib | ...................... 606/159 |
| 4,927,418 A | 5/1990 | Dake et al. | |
| 4,960,415 A | 10/1990 | Reinmuller | |
| 4,968,307 A | 11/1990 | Dake et al. | |
| 5,021,044 A | 6/1991 | Sharkawy | |
| 5,250,034 A | 10/1993 | Appling et al. | |
| 5,336,178 A * | 8/1994 | Kaplan et al. | ............... 604/509 |
| 5,425,723 A | 6/1995 | Wang | |
| 5,509,900 A * | 4/1996 | Kirkman | ...................... 604/104 |
| 5,549,626 A * | 8/1996 | Miller et al. | ................. 606/200 |
| 5,643,226 A | 7/1997 | Cosgrove et al. | |
| 5,672,173 A * | 9/1997 | Gough et al. | .................. 606/41 |
| 5,713,853 A * | 2/1998 | Clark et al. | .................. 604/509 |
| 5,800,407 A | 9/1998 | Eldor | |
| 5,800,408 A | 9/1998 | Strauss et al. | |
| 5,957,901 A | 9/1999 | Mottola et al. | |
| 6,074,374 A | 6/2000 | Fulton | |
| 6,159,196 A * | 12/2000 | Ruiz | .......................... 604/500 |
| 6,179,816 B1 | 1/2001 | Mottola et al. | |
| 6,179,828 B1 | 1/2001 | Mottola et al. | |
| 6,524,300 B2 | 2/2003 | Meglin | |
| 6,547,769 B2 | 4/2003 | VanTassel et al. | |
| 7,004,923 B2 * | 2/2006 | Deniega et al. | ............. 604/4.01 |
| 7,048,729 B2 * | 5/2006 | Meglin et al. | ............ 604/890.1 |

* cited by examiner

*Primary Examiner*—Kevin C. Sirmons
*Assistant Examiner*—Bhisma Mehta
(74) *Attorney, Agent, or Firm*—Workman Nydegger (57) ABSTRACT

A catheter assembly for infusion or aspiration of an internal body site includes a catheter comprised of a tubular sidewall extending between a proximal end and an opposing distal end, the sidewall bounding a lumen. At least one port is formed on the catheter so as to communicate with the lumen. At least one filament extends outwardly from the first catheter. The filament is configured to form a fluid pathway within a body of a patient for fluid entering or exiting the at least one port of the catheter when the catheter is implanted within the body of the patient.

11 Claims, 8 Drawing Sheets

CATHETER ASSEMBLIES FOR CONTROLLED MOVEMENT OF FLUID

CROSS-REFERENCE TO RELATED APPLICATIONS

Not applicable.

BACKGROUND OF THE INVENTION

1. The Field of the Invention

The present invention relates generally to catheter assemblies used to move fluid within an internal body site.

2. The Relevant Technology

Catheters are ubiquitous in many surgical and clinical procedures. Catheters are used to move fluids between an internal body site and a point outside the body. Catheters can be used to deliver fluids, including medications, or they can be used to evacuate fluids from a wound created by surgery, trauma, or disease. Typically, catheters are connected to a reservoir for either supplying or collecting the fluid moving between the internal body site and the extracorporeal site.

Catheters are commonly provided in the form of a tube having a central lumen bounded by a sidewall and one or more ports extending through the sidewall that communicate between the lumen and an exterior surface of the catheter. Other catheters known in the art simply use the terminus of the lumen at the distal end of the catheter as a port. Fluid is moved between the lumen and the internal body site through the ports by application of a pressure to the lumen. The applied pressure is less than the pressure at the internal body site when aspiration is desired, and the applied pressure is greater than the pressure at the internal body site when infusion is desired.

One example of the use of a catheter is the performance of surgical site infusion or aspiration. After the completion of a surgical procedure, a catheter is placed through the skin so that the ports of the catheter are located at or peripheral to the operative site. After the surgical incision or wound is closed, the catheter can be used to deliver medication, such as an antibiotic to treat infection or an analgesic to treat pain, to the internal body site. Alternatively, a catheter placed as just described can be used to evacuate blood and other fluid build-up at the internal body site in order to alleviate swelling and pain.

Catheters for infusion and aspiration known in the art do not reliably provide for a complete perfusion of fluid across the intended site of treatment. The portion of the catheter having the ports is surrounded by layers of tissue that collapse around and put pressure on the exterior surface of the catheter, thereby impeding the movement of fluid through some or all of the ports. During infusion or aspiration, the fluid that is forced into or out of the internal body site will preferentially travel along low resistance pathways, such as folds in the tissue layers, open spaces between tissue structures, or places where the tissue layers are held apart by the very catheter used to move the fluid. This means that, during infusion, fluids forced into the internal body site will travel and collect in low resistance pathways and will not flow into areas where tissue layers are compressed together. Similarly, during aspiration, the tendency of fluid to move along low resistance pathways as described will result in fluids trapped in pockets and sinuses that are isolated from other low resistance pathways that connect to the catheter. Thus, there is a need to provide a catheter that can more effectively move fluid across a target area, the target area being the area of body tissues that has suffered surgical insult, trauma, or disease.

Additionally, catheters commonly have multiple ports for fluid ingress and/or egress. However, the ports are typically of a common size and have a common spacing, resulting in different flow rates at each port as the pressure difference between the extracorporeal site and the internal body site decreases along the length of the catheter due to friction loss and pressure drops across ports. The result is a higher flow rate through proximal ports and lower flow rates through distal ports, providing an uneven rate of flow across the target site. Pressure drops between proximal and distal ports may be so great that distal ports have no flow at all. Therefore, a need exists for a catheter that can induce an even movement of fluid across the target area so that the target area is effectively treated.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
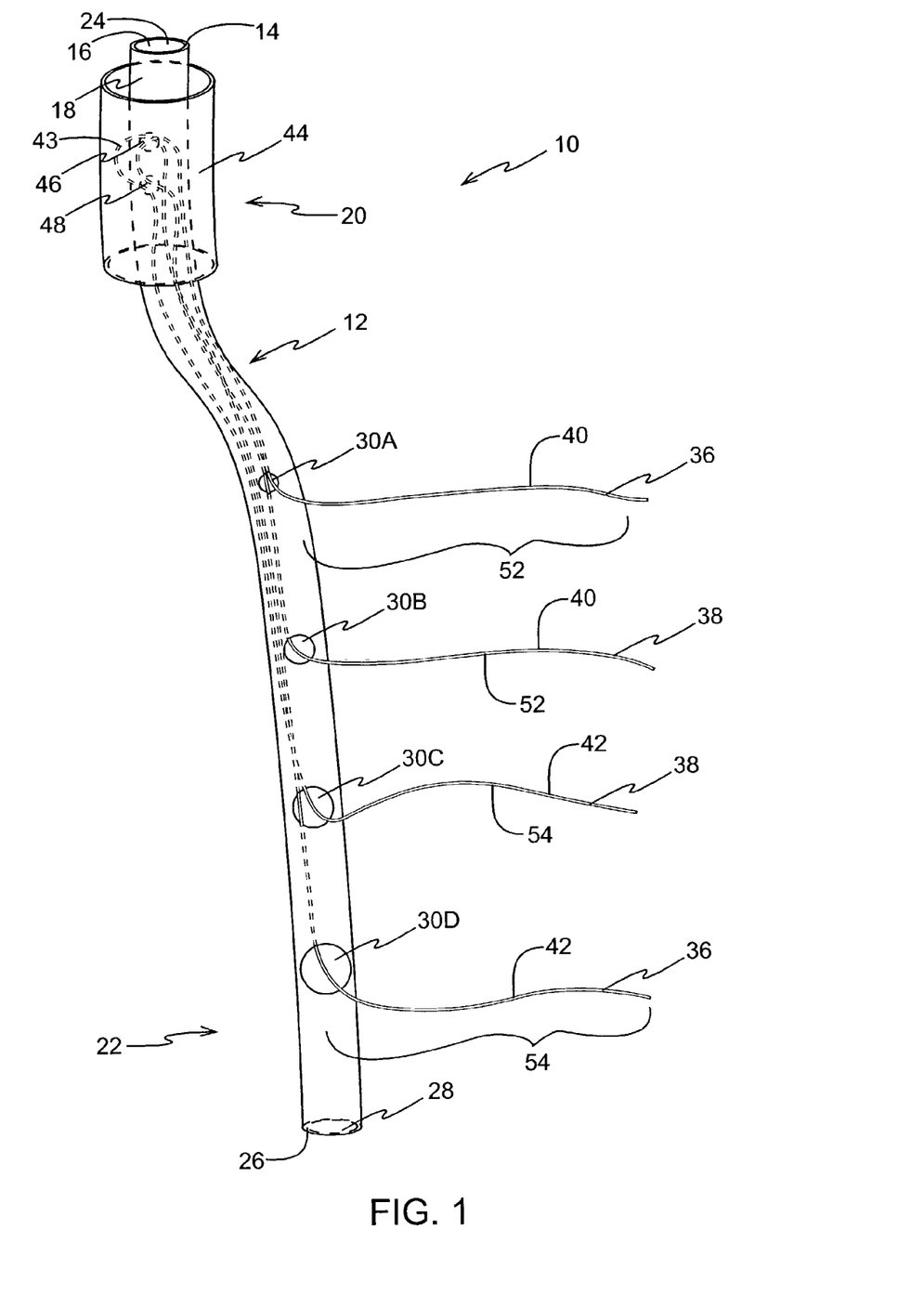
FIG. 1 is an elevated side view of one embodiment of a catheter assembly having filaments projecting from side ports having different sizes.

Depicted in FIG. 1 is one embodiment of a catheter assembly 10 incorporating features of the present invention. Catheter assembly 10 comprises a catheter 12 comprised of a tubular sidewall 14 having an interior surface 16 and an exterior surface 18. Each of surfaces 16 and 18 extend between a proximal end 20 and an opposing distal end 22. Interior surface 16 bounds a lumen 24 that extends along the length of catheter 12. Distal end 22 of catheter 12 terminates at a distal terminus 26. A distal port 28 is formed at distal terminus 26 so as to communicate with lumen 24. Catheter 12 is typically comprised of the same biocompatible polymeric materials as other conventional catheters.

As will be discussed below in greater detail, a first aperture 46 and a spaced apart second aperture 48 extend through sidewall 14 at proximal end 20. Furthermore, a plurality of longitudinally spaced apart side ports 30A-30D are formed on sidewall 14 so as to provide fluid communication between lumen 24 and exterior surface 18. As used in the specification and appended claims, the term "port" refers to side ports and/or distal ports as discussed herein. Catheter 12 is thus configured such that when fluid is injected into catheter 12 from proximal end 20, the fluid flows down through lumen 24 and out through side ports 30 and distal port 28. In alternative embodiments, distal port 28 can be eliminated.

In the embodiment depicted, side ports 30A-D are longitudinally spaced apart. Although not required, in one embodiment it is desirable to have substantially equal flow through each of side ports 30A-30D so that substantially uniform aspiration or infusion can be obtained across a target area. To that end, side ports 30 increase in size from side port 30A to side port 30D. That is, side port 30D is larger than side port 30A.

Flow rate through a port is directly proportional to pressure and also directly proportional to the cross sectional area of the port. As a result of the fluid flowing out of lumen 24 through side ports 30, the fluid pressure within lumen 24 decreases proximal to distal. Accordingly, if all of side ports 30 were the same size, greater fluid would flow out through side port 30A than at 30D because the fluid pressure would be greater at side port 30A. By increasing the size of side ports 30 from 30A to 30D, substantially the same flow rate can be obtained through each of side ports 30A-30D. That is, to create even flow rates, distal ports are made larger in cross sectional area to compensate for the lower pressure. By using fluid mechanics techniques, and in particular applying Bernoulli's equation governing fluid flow, one can select the appropriate port spacing and size for a given pressure difference, flow rate, and friction loss.

In alternative embodiments, any number of side ports 30 can be used having the same or different size. Furthermore, the side ports 30 can be spaced at the same or different longitudinal intervals. In addition, side ports 30 can also be spaced radially and/or longitudinally.

Catheter assembly 10 also comprises two filaments 36 and 38. Each filament 36 and 38 has a first end 40, an opposing second end 42, and a looped portion 43 formed therebetween. Starting with first end 40, filament 36 extends from outside of catheter 12 and into lumen 24 through side port 30A. Filament 36 then extends proximally within lumen 24 where it then passes out through first aperture 46 and then back into lumen 24 through second aperture 48. Looped portion 43 of filament 36 is formed between apertures 46 and 48. Filament 36 then continues distally within lumen 24 and finally projects out through side port 30D. In this embodiment, a free portion 52 of first end 40 of filament 36 projects from side port 36A while a free portion 54 of second end 42 of filament 36 projects from side port 36D. In other words, first end 40 and second end 42 of filaments 36 and 38 outwardly project from the catheter. Free portions 52 and 54 can be of any desired length and can also be the same or different length. Furthermore, free portions 52 and 54 can be trimmed either prior to or at the time of use to the desired length. Either of free portions 52 or 54 can be configured so that the free portion ends at a terminal end that is freely disposed outside of catheter 12 while the catheter 12 is being implanted.

Similar to filament 36, filament 38 enters lumen 24 through side port 30B, extends in and out of apertures 46 and 48, and then exits lumen 24 through side port 30C. In one embodiment, filaments 36 and 38 are comprised of conventional medical grade suture having a diameter in a range between about 0.25 mm to about 1 mm. In alternative embodiments, filaments 36 and 38 can comprise any biocompatible monofilament, such as a polymeric line, or braided fibers, or any other form of line having any desired diameter or cross sectional shape, such as a round, ellipsoid, rectangular, splined, or star shape. The filaments disclosed herein can be metallic or non-metallic. Furthermore, different filaments can be made of different materials having different sizes, and can be made solid or hollow.

In one embodiment of the present invention, means are provided for securing filaments 36 and 38 to catheter 12. By way of example and not by limitation, a retainer 44 is provided that encircles proximal end 20 of catheter 12. Retainer 44 is tightly constricted around catheter 12 so that loop portions 43 of filaments 36 and 38 are held by frictional engagement between retainer 44 and exterior surface 18 of catheter 12.

In one embodiment, retainer 44 comprises a shrink wrapped tube constricted around catheter 12. In other embodiments, retainer 44 comprises tube or flat sheet of material that is welded, adhered or otherwise secured over loop portions 43 of filaments 36 and 38. In these embodiment, retainer 44 also functions to seal apertures 46 and 48 so that no significant amount of fluid passes therethrough. In other embodiments of the means for securing, clamps, crimps, or other mechanical devices can be used to secure filaments 36 and 38 to catheter 12.

During use, distal end 22 of catheter 12 is subcutaneous implanted within a body site of a patient. As noted above, as catheter 12 is implanted, the terminal ends of either of free portion 52 or 54 can remain freely disposed outside of catheter 12 while catheter 12 is being implanted. Proximal end 20 of catheter 12 is disposed outside of the body of the patient so as to allow access thereto. Free portions 52 and 54 of filaments 36 and 38 are selectively positioned within the body site so as to provide desired infusion or aspiration of a fluid at a target site. That is, as a result of filaments 36 and 38 spreading apart the tissue laying thereagainst, each free portion 52 and 54 of filaments 36 and 38 forms a fluid pathway of low resistance directly along the exterior surface thereof In turn, these fluid pathways are in fluid communication with corresponding side ports 30. Accordingly, by uniformly placing free portions 52 and 54 of filaments 36 and 38 over a target site, substantially uniform infusion or aspiration can be performed over the target site. Alternatively, by concentrating the placement of filaments in a given area, infusion or aspiration can be concentrated at that area.

In one embodiment, the filaments are arranged so that an entire target area is covered by a network of the filaments. Furthermore, depending on the density of the network of filaments, many of the isolated pockets of openings between tissue layers can be intersected by the filaments, thus enabling fluid movement between these isolated sites and catheter 12. In this manner, most, if not all, of the target area will be subject to the desired evacuation or delivery of fluid during aspiration or infusion procedures, respectively.

For example, once catheter assembly 10 is implanted, catheter assembly 10 can function as an infusion catheter by infusing a fluid into lumen 24 through proximal end 20. The fluid flows distally within lumen 24 and out through each of side ports 30A-30D. At least a portion of the fluid travels along the fluid pathways formed by the free portions 52 and 54 of filaments 36 and 38. Accordingly, by forming a desired distribution of filaments 36 and 38 over a target site, a desired distribution of the infusion fluid can be dispersed throughout the target site. It is appreciated that the fluid can be any type of fluid desired for infusion. By way of example and not by limitation, the fluid can be an antibiotic and/or an analgesic.

In alternative embodiments, catheter assembly 10 can be used as an aspiration catheter. In this embodiment, a relative negative pressure is formed on lumen 24 at proximal end 20. As a result of the relative negative pressure, fluid is drawn into lumen 24 through side ports 30A-30D from the surrounding body site. Again, because of the relative low resistance in the fluid pathways formed by free portions 52 and 54 of filaments 36 and 38, a substantial amount of the fluid is drawn in through ports 30 from along the fluid pathways. As a result, a desired distribution of aspiration of a target site can be obtained.

Although not required, in one embodiment looped portions 43 of filaments 36 and 38 are positioned outside of the body of the patient. In this embodiment, filaments 36 and 38 can be selectively removed or manipulated by simply pulling on looped portions 43.

FIG. 1 is merely one embodiment of how filaments can be mounted to a catheter. It is appreciated that there are numerous alternative embodiments, some of which are discussed below in greater detail, for positioning and securing the filaments thereon. By way of example and not by limitation, in contrast to having a single filament wherein opposing ends thereof project out through different ports, both opposing ends of a single filament can extend through the same port. Furthermore, three or more filaments can extend through the same port so as to provide a plurality of flow paths at a select longitudinal location along catheter 12. Likewise, in contrast to having two filaments, it is appreciated that catheter assembly 10 can include one or three or more filaments. In other words, a plurality of radially and/or longitudinally space apart filaments can outwardly extend from catheter 12.

Figure 2:
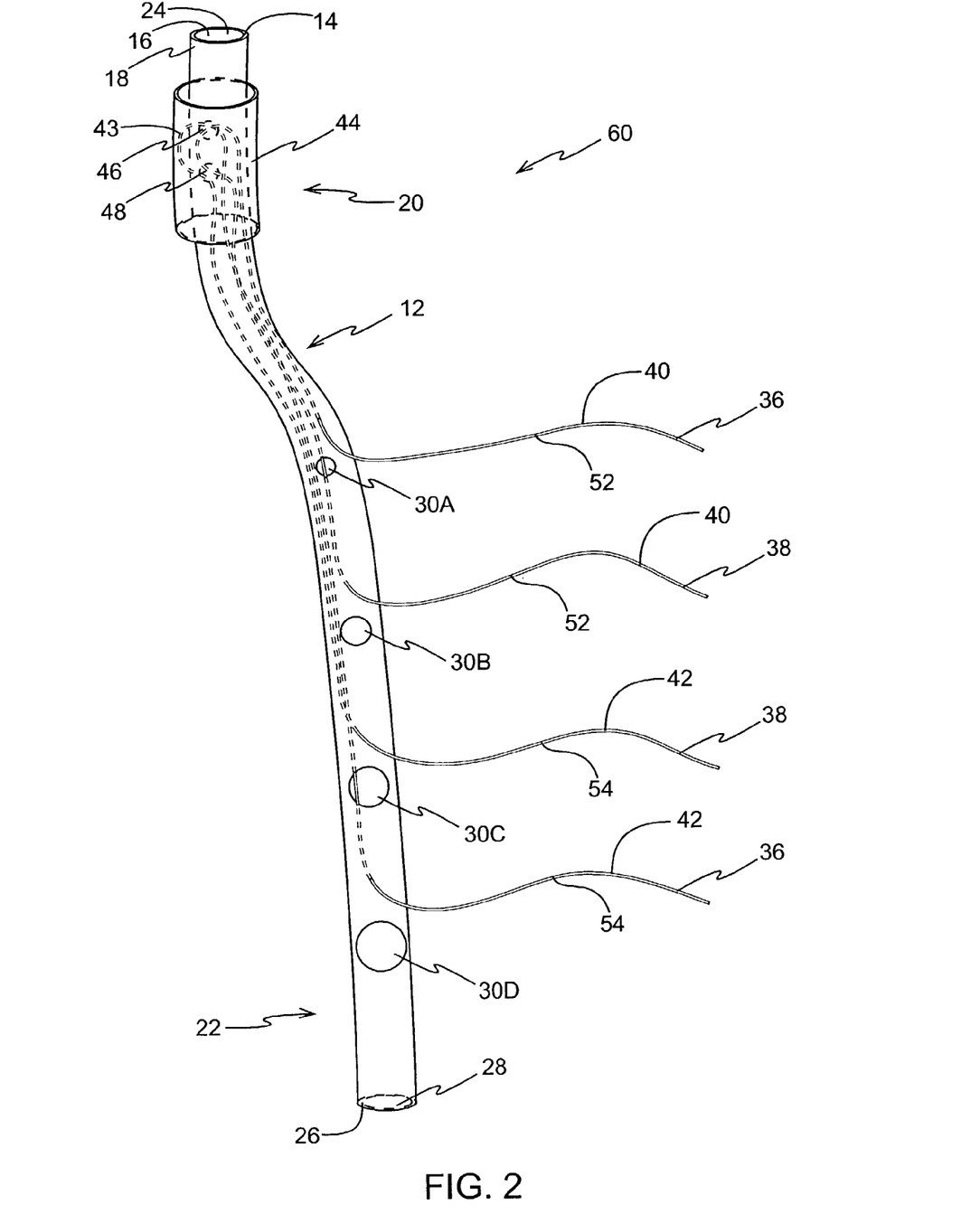
FIG. 2 is an elevated side view of the catheter shown in FIG. 1 having the filaments projecting at a location spaced apart from the side ports.

Furthermore, in contrast to having filaments 36 and 38 loop through apertures 46 and 48 of catheter assembly 10, a discrete filament can be provided for each discrete port. For example, a proximal end of a single filament can extend through aperture 46 and then be secured thereto by retainer 44. To facilitate in the retention thereat, a knot can be formed at the proximal end of the filament, the knot preventing the passage of the filament back through aperture 46. The distal end can then extend down and out through a corresponding side port. In contrast to having the proximal end of each filament secured to the proximal end of catheter 12, the proximal end of each filament can also be secured directly at the distal end of catheter 12 adjacent to a corresponding port. In yet other embodiments, the proximal end of a single filament can freely project out through the proximal end of catheter 12 and then be either freely suspended thereat or be retained using any desired retention structure outside of catheter Depicted in FIG. 2 is an alternative embodiment of a catheter assembly 60. Like elements between the various catheter assemblies disclosed herein are identified by like reference characters. Catheter assembly 60 is substantially the same as catheter assembly 10 except that instead of filaments passing out through corresponding side ports 30, filaments 36 and 38 pass through sidewall 14 at a location spaced apart from corresponding side ports 30. In one embodiment, filaments 36 and 38 pass through sidewall 14 at a distance not greater than 2 mm, 5 mm, or 10 mm from a corresponding side port 30. Other distances can also be used. In this configuration, free portions 52 and 54 of filaments 36 and 38 still form fluid pathways that communicate with side ports 30.

Figure 3:
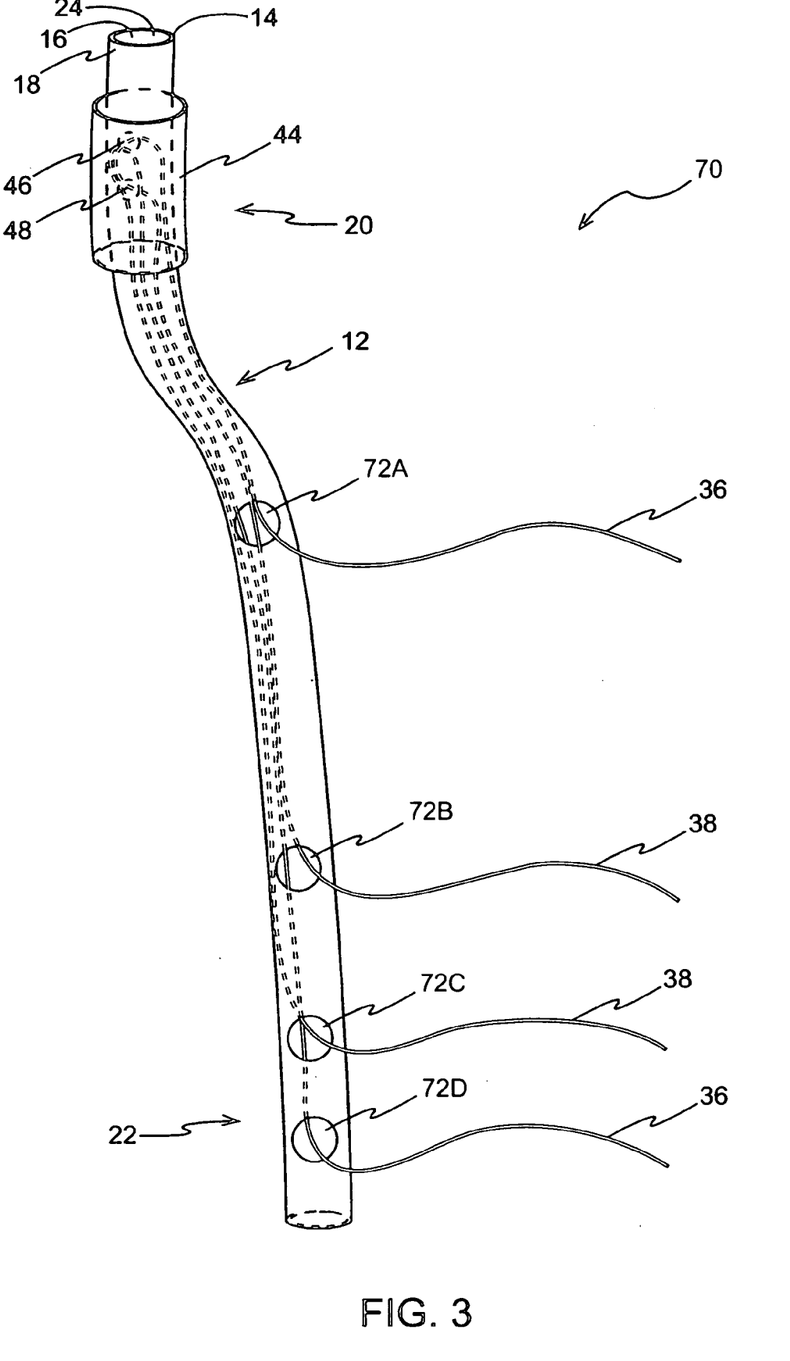
FIG. 3 is an elevated side view of an alternative embodiment of a catheter assembly having filament projecting from side ports of the same size but varied concentration.

Depicted in FIG. 3 is another alternative embodiment of a catheter assembly 70. Catheter assembly 70 comprises catheter 12 having side ports 72A-72D formed thereon in communication with lumen 24. Side ports 72 are distinguishable from side ports 30 in that side ports 72 are all the same size. Furthermore, in contrast to being spaced apart at equal distances, the concentration of side ports increases towards distal end 22. As a result of increasing the concentration of side ports at distal end 52, the flow of fluid into or out of catheter 12 is substantially constant along the length thereof. That is, although the fluid pressure is lower at distal end 22 of catheter 12, as a result of more side ports 74, more fluid is flowing, just at a slower rate.

In view of the foregoing, it is appreciated that one skilled in the art would understand based on the teachings herein that variables such as the size of the ports and the spacing of the ports can be altered in a variety of different combinations so as to produce a substantially uniform flow rate along the length of catheter 12 or, if desired, a variable flow rate of any proportion along the length of catheter 12.

Figure 4:
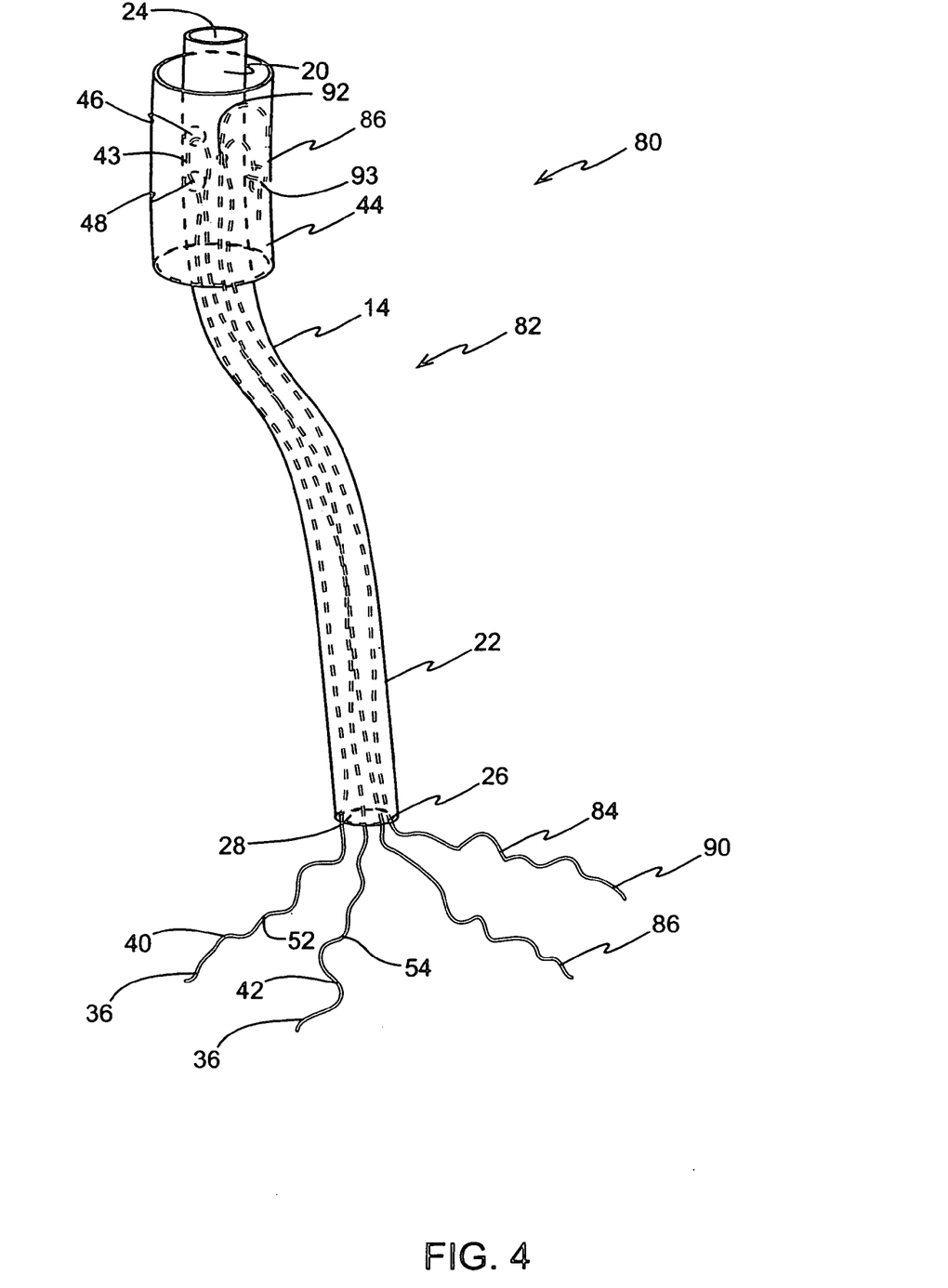
FIG. 4 is an elevated side view of an alternative embodiment of a catheter assembly where each of the filaments project through a distal port.

Depicted in FIG. 4 is yet another alternative embodiment of a catheter assembly 80. Catheter assembly 80 comprises a catheter 82 having tubular sidewall 14 extending between proximal end 20 and opposing distal end 22. In contrast to catheter 12 in FIG. 1, however, catheter 82 does not include side ports 30. Rather, fluid exits from lumen 24 or is drawn into lumen 24 through distal port 28 at distal terminus 26. Filament 36 extends through lumen 24 and loops through apertures 46 and 48.

Catheter assembly 80 also includes discrete filaments 84 and 86. Each filament 84 and 86 has a proximal end 88 and an opposing distal end 90. In contrast to looping through adjacent apertures, each proximal end 88 passes out of lumen 24 through a single aperture 92. Retainer 44, or one of the other means for securing as previously discussed, is used to secure the projecting proximal ends 88 to catheter 82. If desired, a knot 93 can be tied on proximal ends 88 to prevent proximal ends 88 from passing back through aperture 92. Alternatively, proximal ends 88 can be secured to a separate structure that is precluded from passing back through aperture 92. In this embodiment, a free portion of each of the filaments outwardly projects from distal port 28 so as to form flow paths along the lengths thereof.

Figure 5:
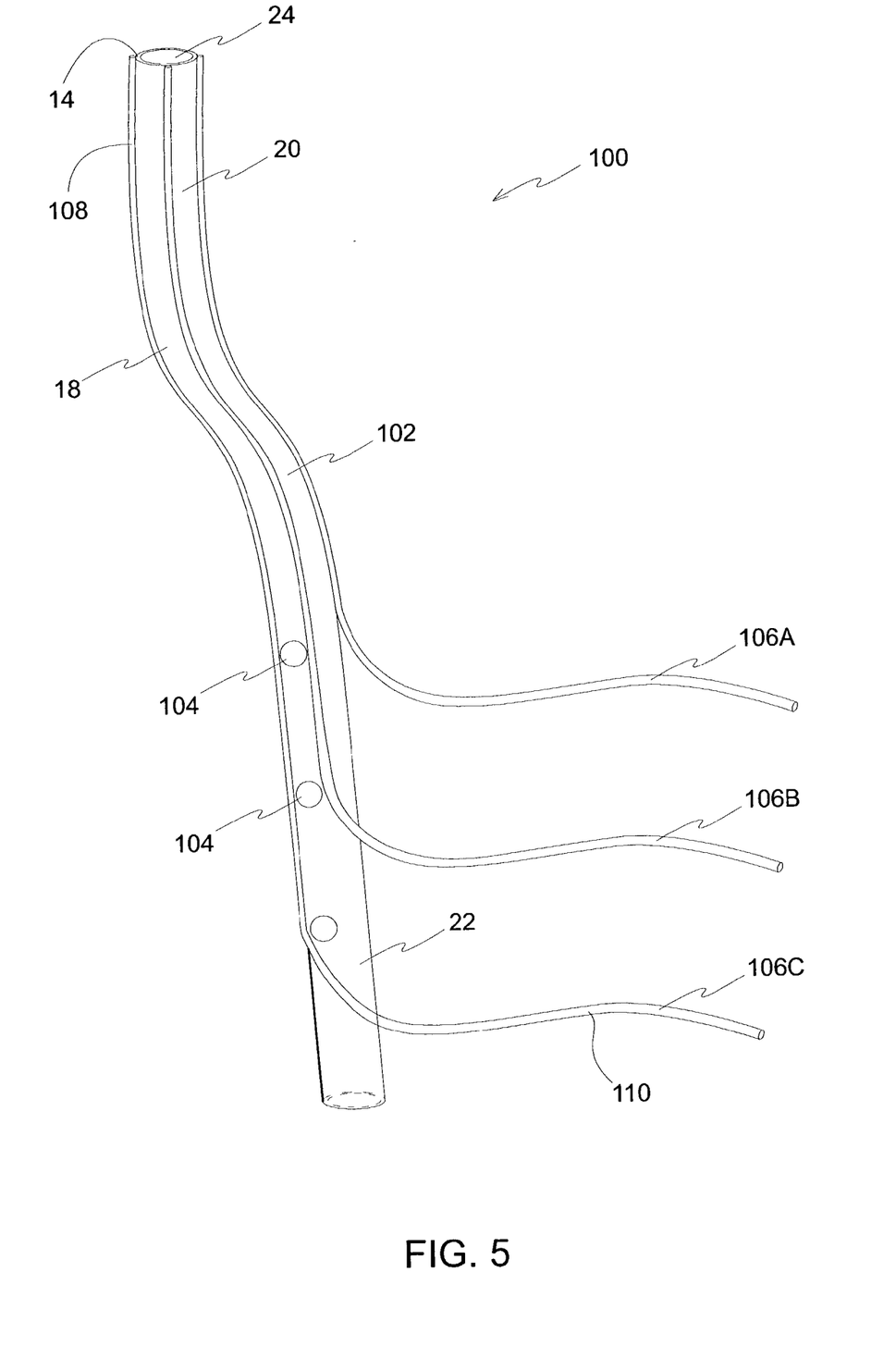
FIG. 5 is an elevated side view of an alternative embodiment of a catheter assembly where the filaments are integrally formed on the exterior surface of the catheter thereof.

Depicted in FIG. 5 is another embodiment of a catheter assembly 100. Catheter assembly 100 includes a catheter 102 which comprises tubular sidewall 14 extending between proximal end 20 and opposing distal end 22. Side ports 104 extend through sidewall 14 so as to communicate with lumen 24. Side ports 104 are of equal size and are longitudinally spaced apart as substantially equal distances.

Integrally formed with catheter 102 are a plurality of filaments 106A-C. Each filament 106 has a proximal end 108 and an opposing distal end 110. In one embodiment, filaments 106 are integrally formed with catheter 102 by being concurrently extruded with catheter 102. Alternatively, catheter 102 and filaments 106 can be injection molded. Filaments 106 are formed on exterior surface 18 of catheter 102 and extend along the length thereof. Once extruded, proximal end 108 of each filament 106 is cut, pulled, or otherwise severed from along catheter 102 up to a point adjacent to a corresponding side port 104. The remainder of each corresponding filament 106 is left secured to catheter 102 so that a separate retaining structure is not required. If desired, distal end 22 of catheter 102 can also be cut back. Filaments 106 function substantially the same way as the other filaments previously discussed.

Figure 6:
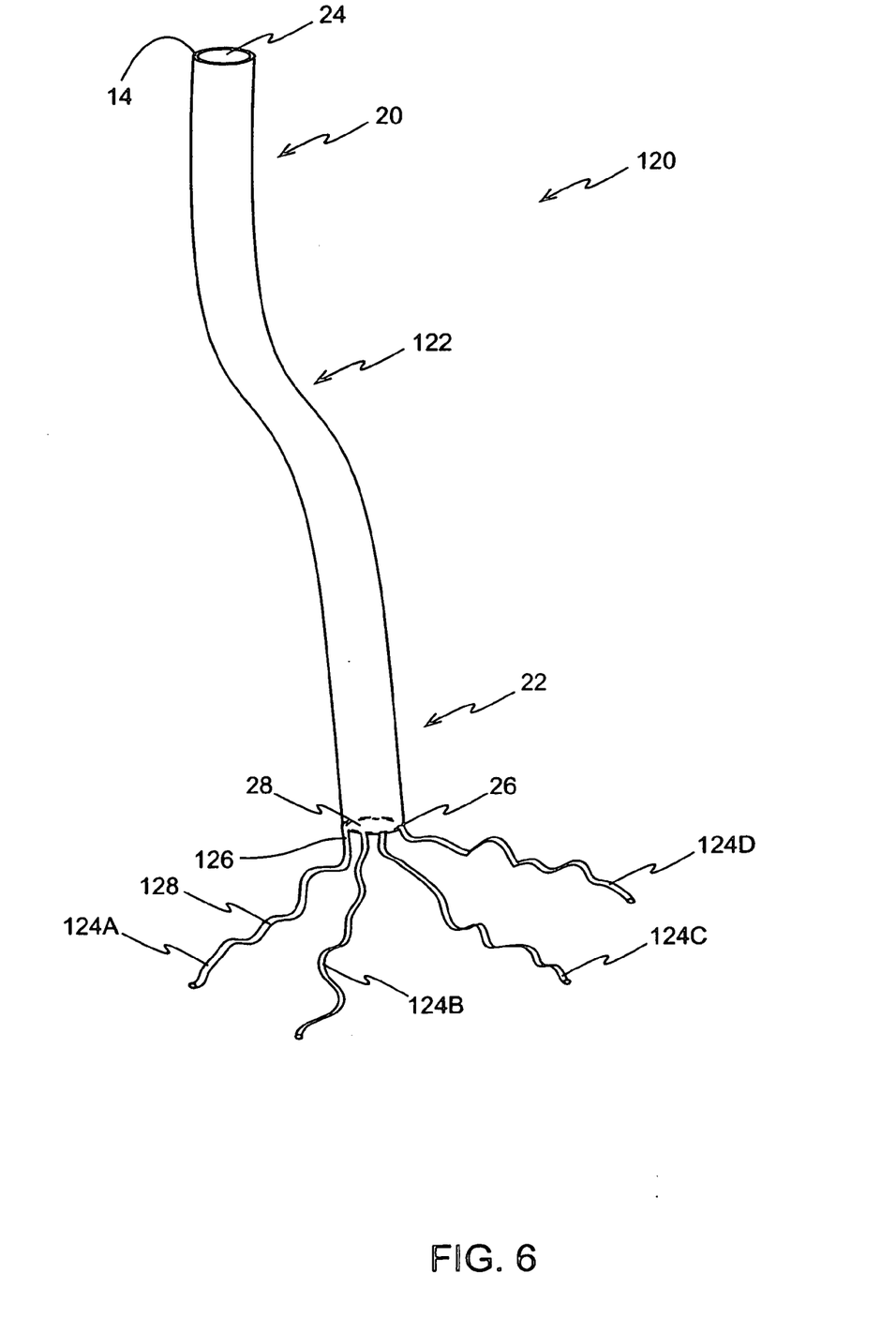
FIG. 6 is an elevated side view of an alternative embodiment of a catheter assembly wherein the filaments are formed at the distal end thereof.

Depicted in FIG. 6 is still another alternative embodiment of a catheter assembly 120. Catheter assembly 120 includes a catheter 122 having tubular sidewall 14 extending between proximal end 20 and distal end 22. Sidewall 14 terminates at distal terminus 26 where distal port 28 is formed in communication with lumen 24.

Catheter assembly 120 comprises a plurality of filaments 124A-D. Each filament 124 has a proximal end 126 and an opposing distal end 128. Proximal end 126 of each filament 124 if integrally molded with distal terminus 26. Filaments 124 can be formed in a variety different fashions. For example, in one embodiment filaments 124 are injection molded with catheter 122. In another embodiment, filaments 124 comprise a distal portion of catheter 122 which has been selectively cut so as to form filaments 124. Filaments 124 form fluid pathways that are in fluid communication with distal port 28. Filaments 124 thus function in substantially the same way as previously discussed filaments and can be used for aspiration or infusion of a fluid.

Figure 7:
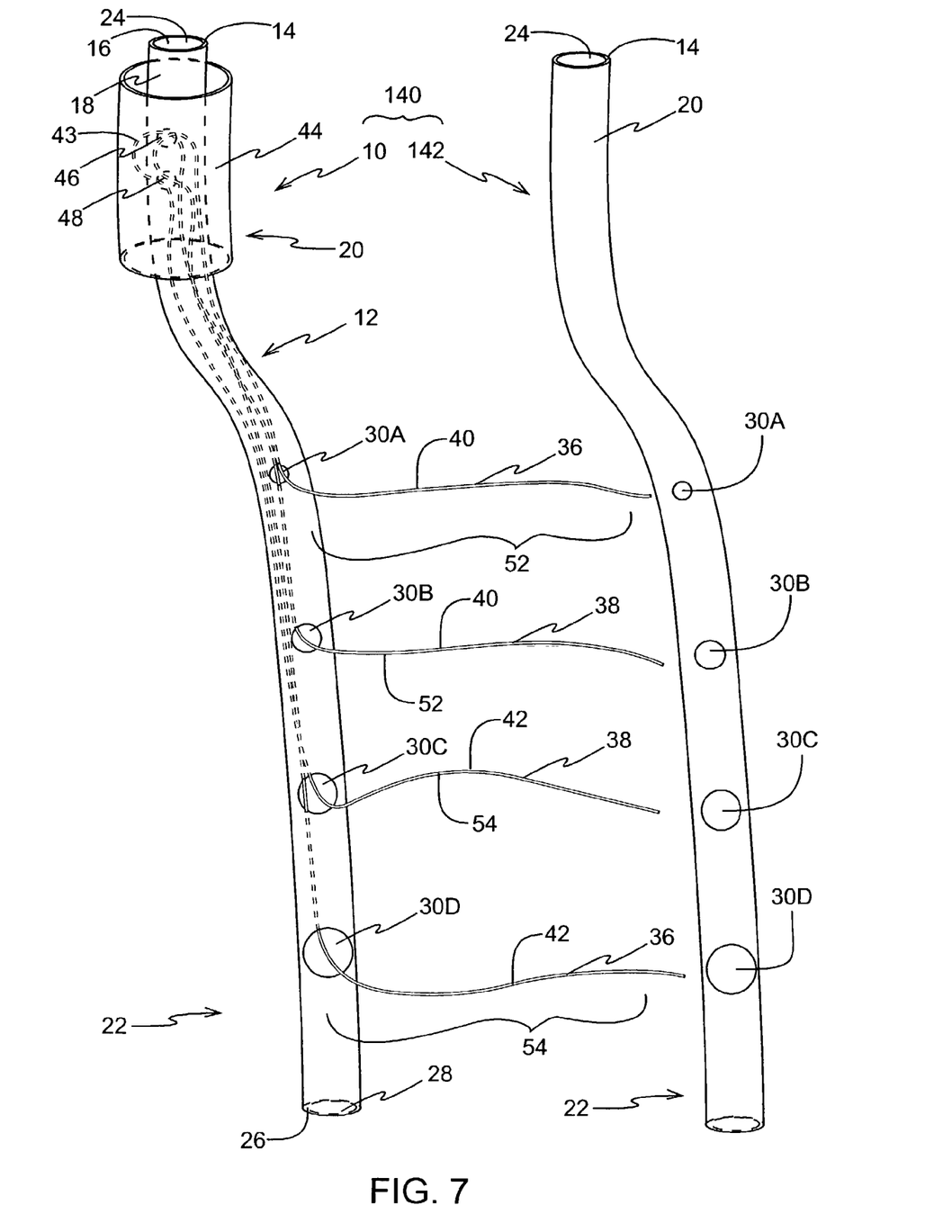
FIG. 7 is an elevated side view of an alternative embodiment of a catheter assembly which comprises the catheter assembly in FIG. 1 with an adjacently disposed second catheter.

Depicted in FIG. 7 is still another embodiment of a catheter assembly 140. Catheter assembly 140 comprises catheter assembly 10 as previously discussed with regard to FIG. 1 and a catheter 142. Catheter 142 has the same configuration as catheter 12 as previously discussed with regard to FIG. 1. During use, catheter assembly 10 is implanted as previously discussed such that filaments 36 and 38 are disposed within the target site. Catheter 142 is disposed at a distance apart from catheter assembly 10 generally on an opposing side of the target site. Filaments 36 and 38 are aligned so as to extend from catheter 12 toward catheter 142 but do not couple with catheter 142. In this configuration, fluid is injected into one of catheter 12 or catheter 142 and then drawn out through the other of catheter 12 or catheter 142. This use of two catheters facilitates a more uniform and directional flow of the fluid across the target site.

Figure 8:
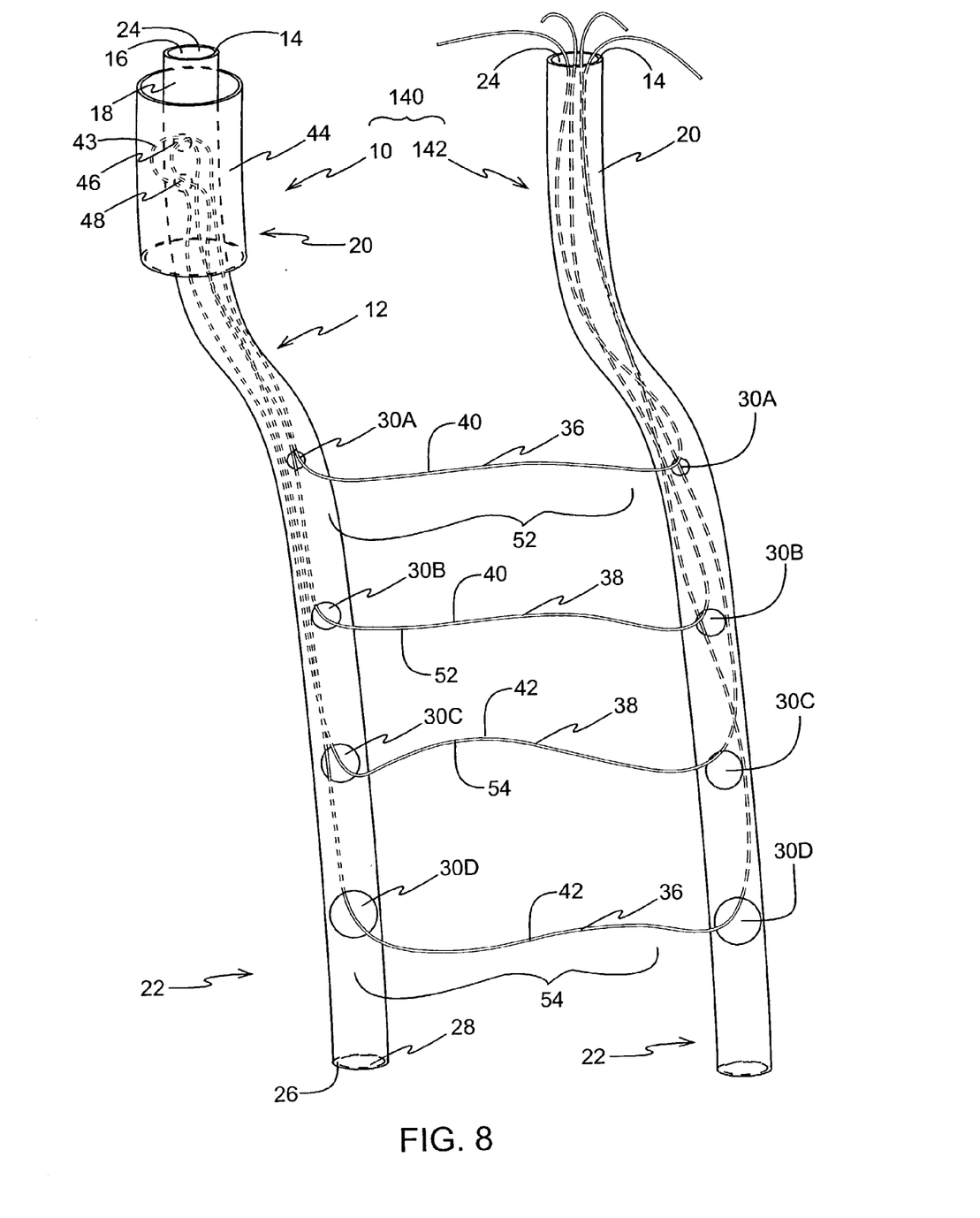
FIG. 8 is an elevated side view of the catheter assembly shown in FIG. 7 with the filaments extending between the catheters thereof.

In contrast to the embodiment depicted in FIG. 7 where the filaments are spaced apart from catheter 142, in the embodiment depicted in FIG. 8, filaments 36 and 38 extend into ports 30A-30D of catheter 142. The filaments can be secured to catheter 142 in any of the same fashions as previously discussed. Connecting the filaments directly between the catheters produces a more direct fluid pathway between the catheters. Again, the catheters are disposed so that the fluid flowing along the filaments pass through the target site so as to uniformly or otherwise infuse the body site.

The present invention may be embodied in other specific forms without departing from its spirit or essential characteristics. For example, above are described various alternative examples of different catheter assemblies. It is appreciated that various features of the different catheter assemblies can be mixed and matched to form a variety of other alternatives. As such the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A catheter assembly for infusion or aspiration of an internal body site, the catheter assembly comprising:
   a first catheter comprised of a tubular sidewall extending between a proximal end and an opposing distal end, the sidewall bounding a lumen, a first port, and a second port, the first port and second port extending through the sidewall of the first catheter so as to communicate with the lumen; and
   a first filament having:
      a first end outwardly extending from the first catheter at or directly adjacent to the first port;
      a second end outwardly extending from the first catheter at or directly adjacent to the second port;
      a looped portion disposed between the first end and the opposing second end that extends out through the sidewall of the first catheter; and
      a remainder portion disposed within the lumen of the first catheter.

2. A catheter assembly as recited in claim 1, wherein the first filament is non-metallic.

3. A catheter assembly as recited in claim 1, wherein the first end of the first filament outwardly extends from the first catheter at a distance of 10 mm or less from the first port.

4. A catheter assembly as recited in claim 1, further comprising a plurality of longitudinally and/or radially spaced apart ports formed on the sidewall of the first catheter.

5. A catheter assembly as recited in claim 1, wherein the first port and second port are longitudinally spaced apart, the second port being disposed distal of the first port and being larger than the first port.

6. A catheter assembly as recited in claim 1, further comprising a plurality of longitudinally spaced apart ports formed on the sidewall of the first catheter, the concentration of ports increasing toward the distal end of the sidewall.

7. A catheter assembly as recited in claim 1, wherein the first filament extends through the first port.

8. A catheter assembly as recited in claim 1, further comprising a retainer encircling the proximal end of the first catheter and fixedly securing the first filament to the first catheter by frictional engagement.

9. A method for infusion or aspiration of an internal body site, the method comprising:
   implanting a catheter assembly into a body of a patient, the catheter assembly comprising:
      a first catheter comprised of a tubular sidewall having an exterior surface extending between a proximal end and an opposing distal end, the sidewall bounding a lumen, a plurality of ports being formed on the first catheter so as to provide fluid communication between the lumen and the exterior surface of the sidewall, the ports being longitudinally spaced apart along the catheter between the proximal end and the distal end thereof; and
      a plurality of filaments each having a first end and an opposing second end, the second end of each filament outwardly extending from the first catheter at or adjacent to a separate one of the plurality of ports, the first end of each filament outwardly extending from the first catheter at or adjacent to a separate one of the plurality of ports, the first end and the second end of each filament each extend from the first catheter at or adjacent to separate ports, the catheter assembly being implanted so that the plurality of ports and the plurality of filaments are subcutaneously disposed at an internal body site of the patient, the second end of each filament having a terminal end freely disposed outside of the first catheter while the catheter assembly is being implanted; and
   infusing a fluid into the first catheter so that the fluid flows out through at least one of the ports and along at least a portion of a fluid pathway formed by at least one of the filaments or aspirating a fluid from the first catheter so that fluid is drawn from the internal body site along at least a portion of the fluid pathway formed by the at least one of the filaments and into at least one of the ports.

10. A method as recited in claim 9, further comprising implanting a second catheter into the body of the patient, the second catheter being comprised of a tubular sidewall extending between a proximal end and an opposing distal end, the sidewall bounding a lumen, a port being formed on the second catheter so as to communicate with the lumen, the second catheter being subcutaneously disposed at a location spaced apart from the plurality of filaments but sufficiently close thereto such that fluid flowing into or out of the port of the second catheter passes along at least a portion of the fluid pathway formed by at least one of the filaments.

11. A method as recited in claim 10, wherein at least one of the filaments extends from the first catheter to the second catheter.

* * * * *

UNITED STATES PATENT AND TRADEMARK OFFICE
CERTIFICATE OF CORRECTION

PATENT NO. : 7,326,196 B2
APPLICATION NO. : 10/270091
DATED : February 5, 2008
INVENTOR(S) : Raymond E. Olsen et al.

It is certified that error appears in the above-identified patent and that said Letters Patent is hereby corrected as shown below:

Column 4: Line 26: ((DELETE)) "embodiment" and (ADD) --embodiments--

Column 4: Line 31: ((DELETE)) "subcutaneous" and (ADD) --subcutaneously--

Column 4: Line 44: (ADD) --.-- after "thereof"

Column 5: Line 37: ((DELETE)) "space apart" and (ADD) --spaced apart--

Column 6: Line 53: ((DELETE)) "as" and (ADD) --at--

Column 7: Line 13: (ADD) --of-- after "variety"

Signed and Sealed this

Twenty-second Day of July, 2008

JON W. DUDAS
*Director of the United States Patent and Trademark Office*